(12) United States Patent
Henry

(10) Patent No.: US 10,113,943 B2
(45) Date of Patent: Oct. 30, 2018

(54) MULTIPLE AGGRESSOR HAIR ASSESSMENT METHOD

(71) Applicant: Conopco, Inc., Englewood Cliffs, NJ (US)

(72) Inventor: Liam Ward Henry, Warrington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 44 days.

(21) Appl. No.: 15/165,154

(22) Filed: May 26, 2016

(65) Prior Publication Data

US 2016/0356684 A1 Dec. 8, 2016

Related U.S. Application Data

(60) Provisional application No. 62/169,678, filed on Jun. 2, 2015.

(51) Int. Cl.
G01N 3/02 (2006.01)
G01N 33/483 (2006.01)
G01N 33/36 (2006.01)
A45D 7/04 (2006.01)
A45D 44/00 (2006.01)

(52) U.S. Cl.
CPC ............ *G01N 3/02* (2013.01); *A45D 7/04* (2013.01); *A45D 44/005* (2013.01); *G01N 33/365* (2013.01); *G01N 33/4833* (2013.01); *A45D 2044/007* (2013.01)

(58) Field of Classification Search
None
See application file for complete search history.

(56) References Cited

U.S. PATENT DOCUMENTS

| | | | | |
|---|---|---|---|---|
| 4,705,681 | A * | 11/1987 | Maes | A61K 8/42 424/59 |
| 2017/0157011 | A1 * | 6/2017 | Punyani | A61K 8/042 |
| 2018/0049970 | A1 * | 2/2018 | Stella | A61K 8/922 |
| 2018/0092825 | A1 * | 4/2018 | Stella | A61K 8/85 |

FOREIGN PATENT DOCUMENTS

FR 2930647 A1 * 10/2009 ......... G01N 33/5088

* cited by examiner

Primary Examiner — Andre Allen
(74) Attorney, Agent, or Firm — Karen E. Klumas

(57) ABSTRACT

A method of comparatively evaluating the efficacy of a series of hair products, the method comprising, in any order, the steps of applying each individual product or product system to an individual test hair switch; each hair switch being subjected to the same regime of two or more aggressors, once a day for 4 or more days; and the condition of the switches being assessed and compared.

7 Claims, No Drawings

MULTIPLE AGGRESSOR HAIR ASSESSMENT METHOD

FIELD OF THE INVENTION

The present invention is concerned with a method of assessing hair products. More particularly, the present invention is concerned with an enhanced comparison and greater differentiation between hair samples treated with different products.

BACKGROUND OF THE INVENTION

In the hair care industry it is often desired to test the efficacy of a product. Current methods generally comprise treating a hair sample with a hair product, subjecting the hair sample to a single aggressor and measuring the resulting change in condition.

It has now been found that; subjecting a hair sample to multiple aggressors, on multiple days, and measuring the condition, will provide enhanced differentiating data on the condition of the hair and therefore provide a superior assessment of the efficacy of any products used in the hair. Furthermore this is a more realistic and consumer relevant assessment of the condition of hair and efficacy of hair care products.

SUMMARY OF THE INVENTION

A method of comparatively evaluating the efficacy of a series of hair products, the method comprising, in any order, the steps of;
Applying each individual product or product system to an individual test hair switch;
Each hair switch being subjected to the same regime of two or more aggressors, once a day for 4 or more days; and
The condition of the switches being assessed and compared.

DETAILED DESCRIPTION OF THE INVENTION

The present invention is a method of comparatively evaluating the efficacy of a series of products. The method provides more differentiating data to make a comparison between products. The method comprises the steps of; applying products to hair switches, subjecting the hair switches to the same cycles of two or more aggressors, once a day for 4 or more days and assessing the condition of the switches.

The steps may be carried out in any order, for example the hair switches may be treated every day of the method and the condition accessed every 3 days of the method.

By the term 'products' is meant any chemical composition suitable for application to hair. The products may be 'rinse-off' compositions or 'leave-on' compositions. Preferably the products are hair products for example shampoos, conditioners, dyes, leave on treatments, styling products etc.

'Products' refer to either one product used alone or a product system, which comprises two or more products for use in combination with each other. For example a hair product system may comprise a shampoo and a conditioner.

'Evaluating the efficacy' may be the evaluation of any effect caused by a product. This may be a desired effect or an undesired effect. The effect is measured by the condition of the hair.

Aggressors

By an aggressor is meant something that changes the physical condition or integrity of a fibre, internally or externally, or that effects the perceived condition of the fibre. Aggressors may not always cause physical damage to the structure, they can simply affect the look e.g. static or frizz caused by water contacting the hair. The changes may be permanent or temporary.

The hair samples are subjected to 2 or more aggressors, preferably 3 or more aggressors and most preferably 4 or more aggressors each day of the method.

The selected aggressors to be carried out on a day of the method are referred to as a cycle of aggressors. The aggressors may be carried out in any order in a cycle and the order may vary on different days of the method. The selected aggressors may vary on each day of the method or stay the same throughout the method.

Preferably a hair switch is subjected to the same aggressors in the same order every day of method.

Aggressors may preferably be selected to reflect a particular experience or lifestyle choice that a consumer's hair is subjected to for example swimming, sun bathing, styling, hot humid atmosphere, pollution in the atmosphere, colouring, heat styling, etc.

Aggressors may preferably be selected to reflect the climatic conditions of a certain geographical location for example, any combination of two or more of; dry66666666, precipitation (varying levels of), humidity, high UV, high temperature, low temperature, high humidity, wind.

Examples of suitable aggressors may be selected from; colouring, bleaching, brushing or combing, heat styling, blow drying, humidity, pollution in the atmosphere, hard or soft water, UV light, wind, rain, various other weather types, climatic changes (e.g. going from high to low heat or humidity quickly), chlorine/swimming pool water, salt/sea water, backcombing, sweating, perming, chemical treatment (for example chemical straightening, relaxing etc.), exerting friction on the hair.

Preferred aggressors include; colouring, bleaching, brushing or combing, heat styling, humidity, pollution, hard or soft water, UV light, wind, rain, various other weather types, climatic changes (e.g. going from high to low heat or humidity quickly), chlorine/swimming pool water, salt/sea water, high temperature.

The most preferred combination of aggressors include; brushing or combing, heat styling, humidity, pollution, hard or soft water, UV light, wind, rain, various other weather types, climatic changes (e.g. going from high to low heat/humidity quickly), chlorine/swimming pool water, salt/sea water, high temperature.

Time Period

The method is carried out over a minimum of 4 days, preferably for a minimum of 5 days, most preferably for a period of 7 days or more.

The method may preferably be carried out over a maximum period of 90 days or less.

Assessment of Condition

The condition of the hair switches is assessed at the end of the method. The condition may also be assessed before and during the method.

By condition is meant any measurable feature of the hair. This may be related to the appearance of a single hair fibre or a group of fibres, related to the behaviour of the hair as a single fibre or a group of fibres or a measure of a physical feature or characteristic of the hair. The measure may be of the external or internal condition of the hair fibre or fibres.

Example methods for assessing the condition of the hair are well known to the person skilled in the art and include; ease of wet comb, hair shine, single fibre stress and single fibre extension, breakage on combing/brushing, texture analysis, image analysis, alignment of fibres, volume, colour change and fade, differential scanning calorimetry, dynamic vapour sorption, thermogravimetric analysis, dynamic contact angle measurement, X-Ray fluorescence, protein leaching.

However any measure of the condition of the hair would be suitable.

The Method

Any combination of aggressors, time period and assessment method may be used to obtain the technical advantage of improved differentiating data.

The method may be designed to match a set of aggressors that a consumer may experience over a period of time. For example a 7 day holiday to a certain geographical location with a certain climate.

A preferred method would comprise a cycle of aggressors comprising; subjecting switch to hard water, subjecting to UV light and humidity, subjecting to polluted air, subjecting to combing, subjecting to rapid changes in humidity, treating with a hair care product and leaving in high humidity conditions overnight. The cycle is preferably repeated on 14 days. The condition of the hair switch is assessed by any of; breakage from combing, volume, differential scanning calorimetry, texture analysis or ease of wet combing.

Another preferred method would comprise a cycle of aggressors comprising; subjecting switch to chlorine water, subjecting to UV light and wind, subjecting to ocean salt water, subjecting to UV light and wind, subjected to combing, treating with a hair care product and leaving in high humidity conditions overnight. The cycle is preferably repeated on 14 days. The condition of the hair switch is assessed at the end by breakage on combing.

EXAMPLES

A comparison was made between hair switches tested according to an embodiment of the inventive method, and compared to hair switches tested according to a standard method of damaging hair switches. For both methods a comparison was made between treatment with an inferior hair treatment and a superior hair treatment.

The inferior hair treatment was a basic shampoo and the superior hair treatment was a shampoo and conditioner system.

Protocol for Inventive Damage Cycle

Virgin hair switches where treated once a day for 14 days following the steps of;

The hair switches were soaked in 3.0 mg/L chlorinated water solution for 30 minutes Removed and patted dry Placed in weather chamber (Atlas S3000 Xenon Weather Ometer). The switches where spun and subjected to light of wave length 340 nm for 1 hour. The side of the switch subjected to the UV light was the same side that any latter measurements were performed on.

Soaked in ocean salt water with a salinity level of 32-35% (Tropic Marine® Sea Salt 35 ml/L) solution for 30 minutes.

Removed and patted dry

Placed in weather chamber (Atlas S3000 Xenon Weather Ometer). The switches where spun and subjected to light of wave length 340 nm for 1 hour. The side of the switch subjected to the UV light was the same side that any latter measurements were performed on.

Using an Automated Combing Device, the switches were combed 200 times at a speed of 55 passes through the switch a minute.

The switches were then treated with the selected product/s;

If Treated with a Shampoo;

The amount of product used was 1 g of product per 1 g of hair.

The switches were wetted, half the shampoo applied, rinsed, other half of the shampoo applied, rinsed, excess water removed, combed to remove tangles and excess water removed.

If Treated with a Conditioner

The amount of product used was 0.2 g of product per 1 g of hair.

The switches were wetted, conditioner applied, rinsed, excess water removed, combed to remove tangles and excess water removed.

The switches were placed in a humidity chamber at 30° C., 80% relative humidity, overnight to dry and removed in the morning.

On days that aggressors could not be performed (i.e. weekends) the switches were left in conditions of 20° C., 50% humidity. These days were not counted as part of the method.

Protocol for Standard Damage Cycle

Using an Automated Combing Device, the switches were combed 200 times at a speed of 55 passes through the switch a minute.

The switches were then treated with the selected product or water;

Then left in conditions of 20° C., 50% humidity until the next day.

Protocol for Assessment of Condition of Hair

The condition of each hair sample was assessed by breakage on combing using an Automated Combing Device. Each hair switch was combed 1000 times w at a speed of 55 passes through the switch a minute. The number of broken hair fibres in a collecting tray bellow were counted and recorded in table 1.

TABLE 1

Number of hairs shed on combing each day of the method

| | A<br>Inferior<br>product | B<br>Superior<br>product | 1<br>Inferior<br>product | 2<br>Superior<br>product |
| --- | --- | --- | --- | --- |
| Day 4 | 41 | 3 | 46 | 2 |
| Day 7 | 44 | 3 | 65 | 2 |
| Day 14 | 78 | 2 | 94 | 2 |

TABLE 2

Number of hairs shed on combing cumulative through the method

| | A<br>Inferior<br>product | B<br>Superior<br>product | 1<br>Inferior<br>product | 2<br>Superior<br>product |
| --- | --- | --- | --- | --- |
| Day 4 | 41 | 3 | 46 | 2 |
| Day 7 | 85 | 6 | 111 | 4 |
| Day 14 | 163 | 8 | 205 | 6 |

Samples A and B are treated according to the standard damage cycle. Samples 1 and 2 are treated according to the inventive test cycle.

The data shows a clear benefit of the inventive method of providing an enhanced comparison method. The difference in performance of products treated using the inventive method is greater than the difference in products using a current method. The larger differentiation provides an enhanced comparison and greater insight into the efficacy of the products.

The invention claimed is:

1. A method of comparatively evaluating the efficacy of a series of hair products, the method comprising, in any order, the steps of;
  applying each individual product or product system to an individual test hair switch;
  subjecting each hair switch to the same regime of two or more aggressors, once a day for 4 or more days; and
  assessing and comparing a condition of the switches that have been treated with the product or product system and subjected to said regime,
wherein the individual product or product system is selected from the group consisting of shampoos, conditioners, and styling products, and the condition is a measurable physical feature or characteristic of the hair switches.

2. A method according claim 1, wherein the two or more aggressors are selected from colouring, bleaching, brushing or combing, heat styling, blow drying, humidity, pollution in the atmosphere, hard or soft water, UV light, wind, rain, various other weather types, climatic changes, chlorine/swimming pool water, salt/sea water, backcombing, sweating, perming, chemical treatment, exerting friction on the hair.

3. A method according claim 1, wherein the aggressors are representative of the average climatic conditions of a particular geographical location.

4. A method according to claim 1 wherein;
  the hair switch or switches are subjected to chlorine, wind, UV, sea salt water and humidity
  every day for 14 days
  the hair switch or switches are treated every day with the selected hair products or product systems
  the hair switch or switches are tested for damage by measuring breakage on combing.

5. A method according to claim 1 wherein the two or more hair switches are subjected to different cycles of aggressors on each day of the period of 4 or more days.

6. Method according to claim 1 for providing advertisement or marketing materials.

7. The method according to claim 1 wherein the measurable feature of the switches is assessed by one or more the following methods: ease of wet comb, hair shine, single fibre stress, single fibre extension, breakage on combing/brushing, texture analysis, image analysis, alignment of fibres, volume, colour change and fade, differential scanning calorimetry, dynamic vapour sorption, thermogravimetric analysis, dynamic contact angle measurement, X-Ray flourescence, and protein leaching.

* * * * *